(12) United States Patent
Oyama et al.

(10) Patent No.: US 7,144,843 B2
(45) Date of Patent: Dec. 5, 2006

(54) PEST CONTROLLERS

(75) Inventors: Kazuhiko Oyama, Yokohama (JP); Takeshi Teraoka, Yokohama (JP); Kazumi Yamamoto, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 306 days.

(21) Appl. No.: 10/470,722

(22) PCT Filed: Jan. 31, 2002

(86) PCT No.: PCT/JP02/00788

§ 371 (c)(1), (2), (4) Date: Jul. 31, 2003

(87) PCT Pub. No.: WO02/060901

PCT Pub. Date: Aug. 8, 2002

(65) Prior Publication Data

US 2004/0067852 A1    Apr. 8, 2004

(30) Foreign Application Priority Data

Jan. 31, 2001    (JP)    ............................. 2001-022668

(51) Int. Cl.
*A01N 43/54* (2006.01)
*C07D 487/02* (2006.01)
*C07D 471/14* (2006.01)

(52) U.S. Cl. ................. 504/243; 546/103; 546/64; 546/66; 546/82; 514/287; 514/288

(58) Field of Classification Search ................. 546/66, 546/103, 64, 82; 514/287, 288; 14/288; 504/243
See application file for complete search history.

(56) References Cited

U.S. PATENT DOCUMENTS

| 3,917,838 A | 11/1975 | Bass et al. |
| 4,008,325 A | 2/1977 | Bass et al. |
| 5,508,289 A * | 4/1996 | Michejda et al. ............ 514/287 |
| 6,187,775 B1* | 2/2001 | Michejda et al. ...... 514/253.02 |
| 6,541,483 B1* | 4/2003 | Michejda et al. ............ 514/284 |

FOREIGN PATENT DOCUMENTS

| JP | 55-49378 | 4/1980 |
| JP | 5-59052 | 3/1993 |

OTHER PUBLICATIONS

Wei-Cheng Zhou et al., "Sythesis and Antibacterial Activities of 2-Substituted-6-oxo-8-fluoro-9-nitrogen-containing Heterocycle-6H-imidazo(4,5,1-ij)-quinoline-5-carboxylic Acids and Their Analogues", Journal of Chinese Pharmaceutical Sciences, 7 (2), pp. 62-68, 1998.

Database Caplus Online! Chemical Abstracts Service, Colombus, Ohio, U.S., Barbara E. Halcrow, et al., "Nitration of 4-chloro- and 4-hydroxyquinaldine", XP 002331369, Database accession No. 1945:28504, RN 444609-64-7 & Journal of the Chemical Society, Abstracts, 415-17 Coden: JCSAAZ; ISSN: 0590-9791, 1945.

* cited by examiner

*Primary Examiner*—Sabiha N Qazi
(74) *Attorney, Agent, or Firm*—Wenderoth, Lind & Ponack, L.L.P.

(57) ABSTRACT

An objective of the present invention is to provide a harmful organism control agent that possesses excellent control effect against harmful organisms and can be safely used. The present invention provides a compound of formula (1) or a salt thereof. The present invention also provides a harmful organism control agent comprising the compound of formula (1).

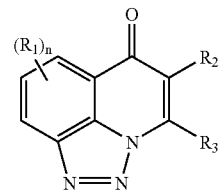

(1)

wherein $R_1$, n, $R_2$, and $R_3$ are as defined in the specification.

6 Claims, No Drawings

PEST CONTROLLERS

BACKGROUND OF THE INVENTION

1. Field of the Invention

The present invention relates to a novel triazoquinolone derivative, a process for producing the same, and a harmful organism control agent comprising said derivative as an active ingredient.

2. Background Art

Many harmful organism control agents have hitherto been reported. However, the number of harmful organism control agents, which do not have satisfactory properties as control agents, among these harmful organism control agents is not small, for example, due to their drawbacks including insufficient efficacy and unsatisfactory safety against organisms, other than the harmful organisms, such as humans and animals.

Accordingly, chemicals, which have satisfactory control effect against harmful organisms and can be used safely, have been desired.

On the other hand, compounds of formula (a) are described in a known literature Journal of Chinese Pharmaceutical Sciences 7 (2), 62, 1998.

So far as the present inventors know, however, compounds having the same structure as the compounds of formula (a) except for the absence of carboxyl at the 5-position, and the effect thereof have not hitherto been known.

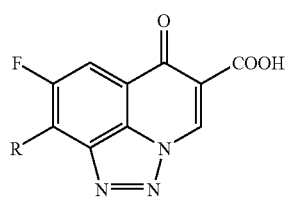

(a)

wherein R represents morpholin-4-yl or pyrrolidin-1-yl.

SUMMARY OF THE INVENTION

The present inventors have now found that triazoquinolone derivatives having a specific structure possess excellent harmful organism control effect. The present invention has been made based on such finding.

Accordingly, an object of the present invention is to provide a harmful organism control agent which possesses excellent control effect against harmful organisms and can be used safely.

According to one aspect of the present invention, there is provided a compound of formula (1) or a salt thereof:

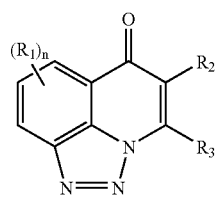

(1)

wherein $R_1$, which may be the same or different, represent(s) a halogen atom; straight chain, branched chain, or cyclic C1–6 alkyl optionally substituted by a halogen atom or hydroxyl; C1–6 alkoxy optionally substituted by a halogen atom or hydroxyl; or nitro, n is an integer of 0 (zero) to 3, $R_2$ represents a hydrogen atom; a halogen atom; or straight chain, branched chain, or cyclic C1–4 alkyl optionally substituted by a halogen atom or hydroxyl, and $R_3$ represents a hydrogen atom; a halogen atom; or straight chain, branched chain, or cyclic C1–12 alkyl optionally substituted by a halogen atom or hydroxyl, or $R_2$ and $R_3$ together may represent —$(CH_2)_m$— wherein m is an integer of 3 or 4.

According to another aspect of the present invention, there is provided a process for producing the compound of formula (1), said process comprising the steps of:

nitrating a compound of formula (2)

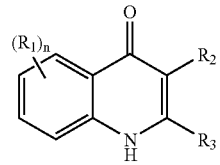

(2)

wherein $R_1$, which may be the same or different, represent(s) a halogen atom; straight chain, branched chain, or cyclic C1–6 alkyl optionally substituted by a halogen atom or hydroxyl; C1–6 alkoxy optionally substituted by a halogen atom or hydroxyl; or nitro, n is an integer of 0 (zero) to 3, $R_2$ represents a hydrogen atom; a halogen atom; or straight chain, branched chain, or cyclic C1–4 alkyl optionally substituted by a halogen atom or hydroxyl, and $R_3$ represents a hydrogen atom; a halogen atom; or straight chain, branched chain, or cyclic C1–12 alkyl optionally substituted by a halogen atom or hydroxyl, or $R_2$ and $R_3$ together may represent —$(CH_2)_m$— wherein m is an integer of 3 or 4, to give a compound of formula (3)

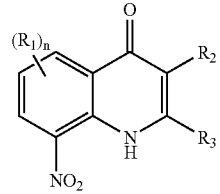

(3)

wherein $R_1$, n, $R_2$, and $R_3$ are as defined in formula (2);

reducing the compound of formula (3) to give a compound of formula (4)

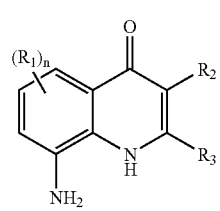

(4)

wherein $R_1$, n, $R_2$, and $R_3$ are as defined in formula (2); and diazotizing the compound of formula (4) to give the compound of formula (1).

Further, according to the present invention, there is provided a harmful organism control agent comprising as an active ingredient at least one of the above compounds or salts thereof.

DETAILED DESCRIPTION OF THE INVENTION

Compounds of Formula (1)

The compounds according to the present invention are compounds of formula (1) (triazoquinolone derivatives) or salts thereof. The compounds of formula (1) or salts thereof possess excellent harmful organism control effect and can be used with high safety. The term "safety" as used herein means that there is little or no toxicity against organisms, other than harmful organisms as control objects, for example, plants as application objects, humans who apply the compound, and animals and vegetables, fishes, birds, beneficial insects and the like which live around the application objects.

In the compounds of formula (1), $R_1$, which may be the same or different, represent(s) a halogen atom; straight chain, branched chain, or cyclic C1–6 alkyl optionally substituted by a halogen atom or hydroxyl; C1–6 alkoxy optionally substituted by a halogen atom or hydroxyl; or nitro. Further, n is an integer of 0 (zero) to 3, preferably 1 or 2.

The term "halogen atom" as used herein means a fluorine, chlorine, bromine, or iodine atom, preferably a fluorine, chlorine, or bromine atom.

In $R_1$, "alkyl" may be in any of straight chain, branched chain, and cyclic forms. The alkyl typically has 1 to 6 carbon atoms. The "alkyl" is optionally substituted by a halogen atom or hydroxyl. Therefore, the "alkyl" may be methyl, ethyl, propyl, butyl, pentyl, or hexyl and preferably represents methyl, trifluoromethyl, ethyl, n-propyl, isopropyl, n-butyl, s-butyl, t-butyl, isobutyl, n-pentyl, isopentyl, neopentyl, or cyclohexyl.

Further, in $R_1$, "alkoxy" may be in any of straight chain and branched chain forms. The alkoxy typically represents 1 to 6 carbon atoms. The "alkoxy" is optionally substituted by a halogen atom or hydroxyl. Specifically, the "alkoxy" may be, for example, methoxy, ethoxy, propoxy, or butoxy and preferably represents methoxy, trifluoromethoxy, or ethoxy.

In the present invention, formula (1) may be represented as formula (1'). In this case, $R_2$ and $R_3$ are as defined in formula (1).

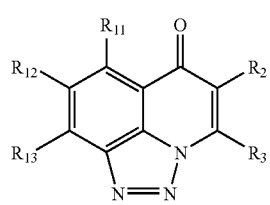

(1')

In this case, $R_{11}$, $R_{12}$, and $R_{13}$ corresponding to $R_1$ in formula (1) may be defined as follows.

Specifically, in formula (1'), $R_{11}$, $R_{12}$, and $R_{13}$ each independently represent a hydrogen atom; a halogen atom; straight chain, branched chain, or cyclic C1–6 alkyl optionally substituted by a halogen atom or hydroxyl; C1–6 alkoxy optionally substituted by a halogen atom or hydroxyl; or nitro.

According to a preferred embodiment of the present invention, $R_{11}$ represents a hydrogen atom; a halogen atom; C1–4 alkyl optionally substituted by a halogen atom; C1–4 alkoxy optionally substituted by a halogen atom; or nitro. More preferably, $R_{11}$ represents a hydrogen atom.

$R_{12}$ preferably represents a hydrogen atom; a halogen atom; straight chain, branched chain, or cyclic C1–6 alkyl optionally substituted by a halogen atom; straight chain, branched chain, or cyclic C1–6 alkoxy optionally substituted by a halogen atom; or nitro. More preferably, $R_{12}$ represents a hydrogen atom, a chlorine atom, methyl, isopropyl, t-butyl, isobutyl, neopentyl, trifluoromethoxy, or nitro.

$R_{13}$ preferably represents a hydrogen atom; a halogen atom; straight chain, branched chain, or cyclic C1–6 alkyl optionally substituted by a halogen atom; straight chain, branched chain, or cyclic C1–6 alkoxy optionally substituted by a halogen atom; or nitro. More preferably, $R_{13}$ represents a hydrogen atom, a chlorine atom, or methoxy.

In the compounds of formula (1), $R_2$ represents a hydrogen atom; a halogen atom; or straight chain, branched chain, or cyclic C1–4 alkyl optionally substituted by a halogen atom or hydroxyl.

In $R_2$, "alkyl" may be in any of straight chain, branched chain, and cyclic forms. The alkyl typically has 1 to 4 carbon atoms. The "alkyl" is optionally substituted by a halogen atom or hydroxyl. Therefore, the "alkyl" may be methyl, ethyl, propyl, or butyl and preferably represents methyl, trifluoromethyl, ethyl, n-propyl, isopropyl, n-butyl, s-butyl, t-butyl, or isobutyl.

In the compounds of formula (1), $R_3$ represents a hydrogen atom; a halogen atom; or straight chain, branched chain, or cyclic C1–12 alkyl optionally substituted by a halogen atom or hydroxyl. Preferably, $R_3$ represents a hydrogen atom or straight chain, branched chain, or cyclic C1–8 alkyl optionally substituted by a halogen atom.

In $R_3$, "alkyl" may be in any of straight chain, branched chain, and cyclic forms. The "alkyl" typically has 1 to 12 carbon atoms, preferably 1 to 8 carbon atoms. The "alkyl" is optionally substituted by a halogen atom or hydroxyl. Therefore, the "alkyl" may represent methyl, ethyl, propyl, butyl, pentyl, hexyl, heptyl, octyl, nonyl, decyl, undecyl, or dodecyl. Preferably, the "alkyl" represents methyl, trifluoromethyl, ethyl, n-propyl, isopropyl, n-butyl, s-butyl, t-butyl, isobutyl, n-pentyl, isopentyl, neopentyl, cyclohexyl, n-heptyl, or n-octyl.

In the compounds of formula (1), as described above, $R_2$ and $R_3$ may represent respective independent groups. Alternatively, $R_2$ and $R_3$ together may represent —$(CH_2)_m$— wherein m is an integer of 3 or 4. Accordingly, $R_2$ and $R_3$ together may form a five- or six-membered ring.

In the present invention, the compounds of formula (1) may form any "salt" without particular limitation, and examples of salts include salts, which are generally usable in agricultural and horiticultural fields, such as hydrochloric acid salts, nitric acid salts, phosphoric acid salts, and acetic acid salts.

The compounds of formula (1) may also take the form of hydrates or solvates. The type of solvent, which forms the solvate, is not particularly limited, and examples of preferred solvents include alcohols such as methanol, ethanol, and isopropanol, and ethers such as tetrahydrofuran. Accordingly, in the present invention, such hydrates and solvates are also embraced in the compounds of formula (1).

Production Process of Compounds of Formula (1)

The compounds of formula (1) according to the present invention may be synthesized by any appropriate process regarding the formation of a bond or the introduction of a substituent. For example, a compound of formula (1) can be produced according to the following scheme.

Scheme:

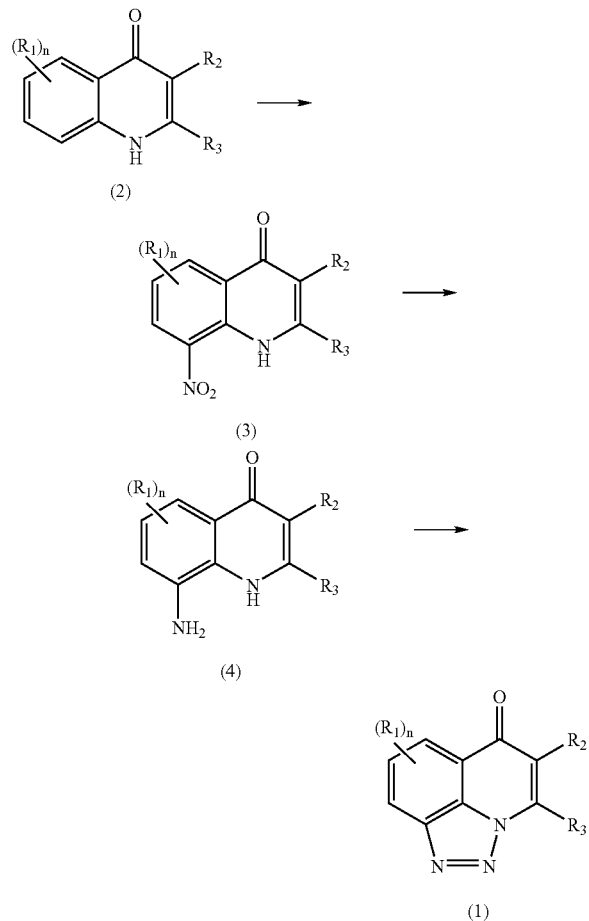

wherein $R_1$, n, $R_2$, and $R_3$ are each as defined in formula (1).

In this scheme, the compound of formula (1) is produced by first nitrating a compound of formula (2) to give a compound of formula (3), reducing the compound of formula (3) to give a compound of formula (4), and diazotizing the compound of formula (4).

The above scheme will be described in more detail.

The compound of formula (2) (quinolone derivative) is first provided. The compound of formula (2) may be provided from any source without particular limitation. For example, the compound of formula (2) may be synthesized by using a substituted aniline, which is commercially available or has been prepared by a conventional method, as a starting compound by a conventional method, for example, a method described in J. Am. Chem. Soc., 70, 2402 (1948) and Tetrahedron Lett., 27, 5323 (1986).

The compound of formula (2) is allowed to react with a nitrating agent at −20 to 25° C. preferably under ice cooling to give a compound of formula (3) as a nitro compound. Nitrating agents usable herein include, for example, mixed acids (nitric acid-sulfuric acid), fuming nitric acid, potassium nitrate, nitronium trifluoromethanesulfonate, nitromethane tetrafluoroborate, and acetyl nitrate.

Next, the compound of formula (4) as an amine compound can be prepared by reducing the nitro group in the compound of formula (3). More specifically, the compound of formula (4) may be prepared by catalytically reducing the nitro group in the compound of formula (3) at −20 to 120° C., preferably 10 to 100° C., in an alcohol or an ether (for example, methanol, ethanol, or dioxane) as a solvent. Alternatively, the compound of formula (4) may be prepared by reducing the nitro group in the compound of formula (3) at −20 to 120° C., preferably 10 to 100° C., in a solvent such as hydrochloric acid or acetic acid in the presence of iron, tin, zinc or the like or in the presence of Raney nickel or the like.

The compound of formula (1) can be prepared by reacting the compound of formula (4) with sodium nitrite at −20 to 20° C. preferably under ice cooling in an acidic solvent, preferably hydrochloric acid, sulfuric acid, or glacial acetic acid, to diazotize the compound of formula (4).

Harmful Organism Control Agent

The compounds of formula (1) possess excellent control effect against harmful organisms. Therefore, the compounds of formula (1) may be used as harmful organism control agents.

Accordingly, according to the present invention, there is provided a harmful organism control agent comprising as an active ingredient at least one of the compounds of formula (1) or salts thereof.

The term "harmful organism" as used herein refers to pest insects or pathogenic fungi, which often or possibly damage agriculture, human life, and the health of humans, and examples thereof include agricultural pest insects, sanitary pest insects, stored grain vermin, clothing pests, house pest insects, and plant pathogenic fungi.

More specifically, examples of such pest insects include: pest insects belonging to Lepidoptera, for example, *Spodoptera litura*, *Mamestra brassicae* L., *Pseudaletia separata* (Walker), green caterpillar, *Plutella xylostella*, and *Spodoptera exigua* (Hubncr); pest insects belonging to Hemiptera, for example, *Myzus persicae*, *Aphis gossypii* Glover, *Laodelphax striatellus* (Fallen), *Nephotettix cincticeps* (Uhler), *Nilaparvata lugens* (Stal), and *Sogatella furcifera*; pest insects belonging to Coleoptera, for example, *Lissorhoptrus oryzophilus*, *Callosobruchus chinensis* (Linne), and *Tenebrio molitor*; Acari, for example, *Tetranychus urticae* Koch, *Tetranychus cinnabarinus*, *Tetranychus kanzawai* Kishida, and *Panonychus citri* McGregor; pest insects belonging to Diptera, for example, *Musca domestica* Linnaeus; and plant parasitic nematode, for example, *Meloidogyne hapla*, *Pratylenchus*, *Aphelenchoides besseyi*, and *Bursaphelenchus xylophilus*.

Further, examples of plant pathogenic fungi include powdery mildew of curcurbits, downy mildew, anthracnose, gray mold, wheat leaf rust, powdery mildew of barley and wheat, and rice blast.

In the present invention, the "control" of harmful organisms includes the prevention of propagation of harmful organisms, not to mention the killing or reduction of harmful organisms, the suppression of growth of harmful organisms, or the removal of harmful organisms from object plant bodies.

Further, comprising "at least one" means that one of the compounds of formula (1) or salts thereof or two or more of the compounds of formula (1) or salts thereof according to the present invention may be contained.

Here "comprising as an active ingredient" embraces the case where a carrier according to the formulation is additionally incorporated and the case where other chemical agents usable in combination with the compound of the present invention are additionally incorporated, not to mention the case where the compound of the present invention as such is used without the addition of any other ingredient.

Accordingly, when the compound of formula (1) is used as an active ingredient of a control agent for harmful organisms, the compound of formula (1) as such may be used. In general, however, the compound of formula (1) may be mixed with suitable solid carriers, liquid carriers, gaseous carriers, surfactants, dispersants and/or other adjuvants for formulations, to prepare any suitable formulation, such as emulsifiable concentrates, liquid formulations, suspension, wettable powder, dust, granules, oil solutions, aerosols, or floables.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitrites, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading the compound of formula (1) include, for example, alkylsulfonic esters, alkyl(aryl) sulfonic acid salts, polyoxyalkylene alkyl(aryl) ethers, polyhydric alcohol esters, and lignin sulfonic acid salts.

Adjuvants usable for improving the properties of formulations include, for example, carboxymethylcellulose, gum arabic, polyethylene glycol, and calcium stearate.

At least two members may be selected from the above group of carriers, group of surfactants, group of dispersants, and group of adjuvants (the selected members may belong to the same group or different groups) and used in combination.

The content of the compound of formula (1) or salt thereof in the control agent for harmful organisms may be properly varied by taking into consideration formulations, application methods and application environment of the control agent and other conditions. The content of the compound of formula (1) is generally 1 to 75% by weight when the control agent is an emulsifiable concentrate; generally 0.3 to 25% by weight when the control agent is dust; generally 1 to 90% by weight when the control agent is wettable powder; and generally 0.5 to 90% by weight when the control agent is granules.

The control agent for harmful organisms according to the present invention is generally used as such or after dilution.

Embodiments of use of the control agent for harmful organisms according to the present invention include, for example, application to plant per se (application to stems and leaves, spraying, misting, atomizing, granule application, application to water surface or the like), application to soil (admixing with soil, drench, application to side stripes or the like), application to surface (coating, dressing, covering or the like), application to seedling boxes, application to field water (application to water surface or application to regular field), seed treatment, and immersion poison baiting.

According to a further aspect of the present invention, there is provided a method for controlling a harmful organism, comprising the step of treating a plant, which has been damaged by a harmful organism or has a fear of being damaged by a harmful organism, with the compound of formula (1) or a salt thereof.

The control agent for harmful organisms according to the present invention may be applied in an amount which may properly vary depending upon, for example, the form of the control agent, application method, the purpose of use, application time, application place, application environment, type of harmful organisms, the state of damage by harmful organisms, and the growth state of plant. For example, however, when the control agent is applied to the surface of the fields where the plant is grown, for example, the amount of the control agent in terms of the amount of the active ingredient is 100 to 5,000 g, preferably 100 to 3,000 g, per hectare.

Further, the control agent for harmful organisms according to the present invention may be used as a mixture, for example, with other bactericides, insecticides, miticides, herbicides, plant growth-regulating agents, or fertilizers.

EXAMPLES

The present invention is further illustrated by the following Examples that are not intended as a limitation of the present invention.

Synthesis of Compounds of Formula (1)

Compounds according to the present invention were synthesized as follows.

Synthesis Example 1

8-t-Butyl-6-oxo-6H-triazo(4,5,1-ij)-quinoline (Compound 6)

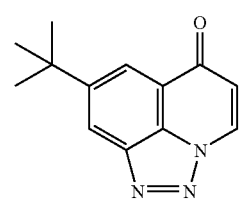

(Compound 6)

6-t-Butylhydroquinolin-4-one (1.00 g) was dissolved in concentrated sulfuric acid (5 ml) to prepare a solution. Concentrated nitric acid (1 ml) was added dropwise to the solution under ice cooling, and the mixture was stirred at the same temperature for 30 min. After the completion of the reaction, the reaction solution was poured into ice water, and the mixture was neutralized with a 10% aqueous sodium hydroxide solution. The resultant precipitate was collected by suction filtration. Next, the collected precipitate was washed with water and was thoroughly dried in a desiccator to give 6-t-butyl-8-nitrohydroquinolin-4-one (953 mg).

Next, the compound 6-t-butyl-8-nitrohydroquinolin-4-one thus obtained was dissolved in tetrahydrofuran (30 ml). To the solution was added 10% palladium-carbon (95 mg). The mixture was stirred under a hydrogen gas stream at room temperature for one hr. After the completion of the reaction, the reaction solution was subjected to suction filtration through Hyflo. The filtrate was evaporated in vacuo. The residue was dissolved in water (1 ml) and concentrated hydrochloric acid (0.5 ml). Sodium nitrite (200 mg) was added to the solution under ice cooling. The mixture was stirred for one hr while gradually raising the temperature of the mixture to room temperature. After the completion of the reaction, water was added to the reaction solution, and the mixture was stirred. The mixture was extracted with ethyl acetate to give the target compound. Next, the organic layer containing the target compound was washed with saturated brine and was then dried over anhydrous sodium sulfate. The solvent was removed by evaporation under the reduced pressure. The crude product thus obtained was purified by chromatography on silica gel (Wako Gel C-200, eluted with hexane:ethyl acetate=5:1) to give 274 mg of compound 6 as a light yellow powder (yield: 24.2%).

$^1$H-NMR data of the compound thus obtained are shown in Table 1.

Synthesis Example 2

8-t-Butyl-4-ethyl-5-methyl-6-oxo-6H-triazo(4,5,1-ij)-quinoline (Compound 12)

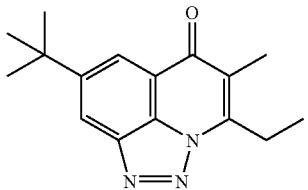

(Compound 12)

6-t-Butyl-2-ethyl-3-methylhydroquinolin-4-one (1.00 g) was dissolved in concentrated sulfuric acid (5 ml) to prepare a solution. Concentrated nitric acid (1 ml) was added dropwise to the solution under ice cooling, and the mixture was stirred at the same temperature for 30 min. After the completion of the reaction, the reaction solution was poured into ice water, and the mixture was neutralized with a 10% aqueous sodium hydroxide solution and was then extracted with ethyl acetate. Next, the organic layer was washed with a saturated aqueous sodium hydrogencarbonate solution and saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=3:1) to give 6-t-butyl-2-ethyl-3-methyl-8-nitrohydroquinolin-4-one (289 mg).

Next, the compound 6-t-butyl-2-ethyl-3-methyl-8-nitrohydroquinolin-4-one thus obtained was dissolved in methanol (10 ml) to prepare a solution. To the solution was added 10% palladium-carbon (29 mg). The mixture was stirred under a hydrogen gas stream at room temperature for one hr. After the completion of the reaction, the reaction solution was subjected to suction filtration through Hyflo. The filtrate was evaporated in vacuo. The residue was dissolved in water (2 ml) and concentrated hydrochloric acid (1 ml). Sodium nitrite (100 mg) was added to the solution under ice cooling. The mixture was stirred for one hr while gradually raising the temperature of the mixture to room temperature. After the completion of the reaction, water was added to the reaction solution, and the mixture was stirred. The mixture was extracted with ethyl acetate to give the target compound. Next, the organic layer containing the target compound was washed with saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=5:1) to give 120 mg of compound 12 as a light yellow powder (yield: 10.8%).

$^1$H-NMR data of the compound thus obtained are shown in Table 1.

Synthesis Example 3

8-s-Butyl-4,5-dimethyl-6-oxo-6H-triazo(4,5,1-ij)-quinoline (Compound 13)

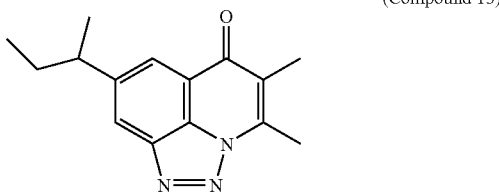

(Compound 13)

6-s-Butyl-2,3-dimethylhydroquinolin-4-one (1.00 g) was dissolved in concentrated sulfuric acid (4 ml) to prepare a solution. Concentrated nitric acid (1 ml) was added dropwise to the solution under ice cooling, and the mixture was stirred at the same temperature for 30 min. After the completion of the reaction, the reaction solution was poured into ice water, and the mixture was neutralized with a 10% aqueous sodium hydroxide solution and was then extracted with ethyl acetate. Next, the organic layer was washed with a saturated aqueous sodium hydrogencarbonate solution and saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=3:1) to give 6-s-butyl-2,3-dimethyl-8-nitrohydroquinolin-4-one (150 mg).

Next, the compound 6-s-butyl-2,3-dimethyl-8-nitrohydroquinolin-4-one thus obtained was dissolved in methanol (10 ml) to prepare a solution. To the solution was added 10% palladium-carbon (15 mg). The mixture was stirred under a hydrogen gas stream at room temperature for one hr. After the completion of the reaction, the reaction solution was subjected to suction filtration through Hyflo. The filtrate was evaporated in vacuo. The residue was dissolved in water (2 ml) and concentrated hydrochloric acid (1 ml). Sodium nitrite (50 mg) was added to the solution under ice cooling. The mixture was stirred for 30 min while gradually raising the temperature of the mixture to room temperature. After the completion of the reaction, water was added to the reaction solution, and the mixture was stirred. The mixture was extracted with ethyl acetate to give the target compound. Next, the organic layer containing the target compound was washed with saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=5:1) to give 44 mg of compound 13 as a light yellow powder (yield: 3.9%).

$^1$H-NMR data of the compound thus obtained are shown in Table 1.

Synthesis Example 4

8-s-Butyl-4-trifluoromethyl-6-oxo-6H-triazo(4,5,1-ij)-quinoline (Compound 14)

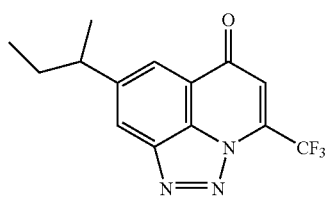

(Compound 14)

6-s-Butyl-2-trifluoromethylhydroquinolin-4-one (1.00 g) was dissolved in concentrated sulfuric acid (4 ml) to prepare a solution. Concentrated nitric acid (1 ml) was added dropwise to the solution under ice cooling, and the mixture was stirred at the same temperature for one hr. After the completion of the reaction, the reaction solution was poured into ice water, and the mixture was neutralized with a 10% aqueous sodium hydroxide solution and was then extracted with ethyl acetate. Next, the organic layer was washed with a saturated aqueous sodium hydrogencarbonate solution and saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=10:1) to give 6-s-butyl-2-trifluoromethyl-8-nitrohydroquinolin-4-one (228 mg).

Next, the compound 6-s-butyl-2-trifluoromethyl-8-nitrohydroquinolin-4-one thus obtained was dissolved in methanol (5 ml) to prepare a solution. To the solution was added 10% palladium-carbon (20 mg). The mixture was stirred under a hydrogen gas stream at room temperature for one hr. After the completion of the reaction, the reaction solution was subjected to suction filtration through Hyflo. The filtrate was evaporated in vacuo. The residue was dissolved in water (2 ml) and concentrated hydrochloric acid (1 ml). Sodium nitrite (100 mg) was added to the solution under ice cooling. The mixture was stirred for 30 min while gradually raising the temperature of the mixture to room temperature. After the completion of the reaction, water was added to the reaction solution, and the mixture was stirred. The mixture was extracted with ethyl acetate to give the target compound. Next, the organic layer containing the target compound was washed with saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=20:1) to give 42 mg of compound 14 as a light yellow powder (yield: 3.8%).

$^1$H-NMR data of the compound thus obtained are shown in Table 1.

Synthesis Example 5

8-t-Butyl-5-chloro-4-methyl-6-oxo-6H-triazo(4,5,1-ij)-quinoline (Compound 21)

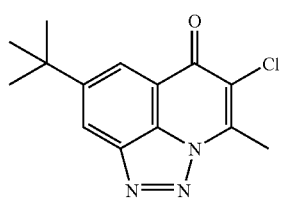

(Compound 21)

6-t-Butyl-3-chloro-2-methylhydroquinolin-4-one (2.00 g) was dissolved in concentrated sulfuric acid (10 ml) to prepare a solution. Concentrated nitric acid (2 ml) was added dropwise to the solution under ice cooling, and the mixture was stirred at the same temperature for 1.5 hr. After the completion of the reaction, the reaction solution was poured into ice water, and the mixture was neutralized with a 10% aqueous sodium hydroxide solution and was then extracted with ethyl acetate. Next, the organic layer was washed with a saturated aqueous sodium hydrogencarbonate solution and saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=3:1) to give 6-t-butyl-3-chloro-2-methyl-8-nitrohydroquinolin-4-one (442 mg).

Next, the compound 6-t-butyl-3-chloro-2-methyl-8-nitrohydroquinolin-4-one thus obtained was dissolved in methanol (15 ml) to prepare a solution. To the solution was added 10% palladium-carbon (45 mg). The mixture was stirred under a hydrogen gas stream at room temperature for one hr. After the completion of the reaction, the reaction solution was subjected to suction filtration through Hyflo. The filtrate was evaporated in vacuo. The residue was dissolved in water (2 ml) and concentrated hydrochloric acid (1 ml). Sodium nitrite (200 mg) was added to the solution under ice cooling. The mixture was stirred for one hr while gradually raising the temperature of the mixture to room temperature. After the completion of the reaction, water was added to the reaction solution, and the mixture was stirred. The mixture was extracted with ethyl acetate to give the target compound. Next, the organic layer containing the target compound was washed with saturated brine and was then dried over anhydrous sodium sulfate. The solvent was removed by evaporation under the reduced pressure to give a crude product. The crude product thus obtained was purified by chromatography on silica gel (Wako Gel C-200, eluted with hexane:ethyl acetate=10:1) to give 204 mg of compound 21 as a light yellow powder (yield: 9.2%).

$^1$H-NMR data of the compound thus obtained are shown in Table 1.

Other Synthesis Examples

Compounds 1 to 5, 7 to 11, 15 to 20, and 22 to 30 according to the present invention were synthesized from starting compounds shown in Table 1 in the same manner as in Synthesis Examples 1 to 5.

Yields and $^1$H-NMR data of these compounds are shown in Table 1.

TABLE 1

| Compound No. | Starting compound | Yield, % | R₁ | R₂ | R₃ | NMR (ppm), CDCl₃ |
|---|---|---|---|---|---|---|
| 1 | (structure) | 18.1 | 8-t-Bu | CH₃ | CH₃ | 1.49 (9H, s), 2.21 (3H, d, J = 1.0 Hz), 2.94 (3H, d, J = 1.0 Hz), 8.44 (1H, d, J = 1.3 Hz), 8.46 (1H, d, J = 1.3 Hz) |
| 2 | (structure) | 12.3 | 8-H | H | H | 6.52 (1H, d, J = 7.8 Hz), 7.81 (1H, t, J = 7.8 Hz), 8.36 (1H, d, J = 7.5 Hz), 8.48 (1H, d, J = 8.0 Hz), 8.59 (1H, d, J = 7.8 Hz) |
| 3 | (structure) | 9.8 | 8-H | CH₃ | CH₃ | 2.22 (3H, d, J = 1.0 Hz), 2.96 (3H, d, J = 1.0 Hz), 7.74 (1H, dd, J1 = 8.0 Hz, J2 = 7.5 Hz), 8.35 (1H, d, J = 7.5 Hz), 8.42 (1H, d, J = 8.0 Hz) |
| 4 | (structure) | 0.6 | 8-CH₃ | CH₃ | CH₃ | 2.21 (3H, d, J = 0.8 Hz), 2.69 (3H, s), 2.94 (3H, d, J = 0.8 Hz), 8.18 (1H, s), 8.19 (1H, s) |
| 5 | (structure) | 4.4 | 8-H | H | CH₃ | 2.91 (3H, d, J = 1.2 Hz), 6.29 (1H, d, J = 1.2 Hz), 7.76 (1H, t, J = 7.5 Hz), 8.32 (1H, d, J = 7.5 Hz), 8.43 (1H, d, J = 7.5 Hz) |

TABLE 1-continued

| Compound No. | Starting compound | Yield, % | R₁ | R₂ | R₃ | NMR (ppm), CDCl₃ |
|---|---|---|---|---|---|---|
| 6 | | 24.2 | 8-t-Bu | H | H | 1.50 (9H, s), 6.49 (1H, d, J = 7.8 Hz), 8.47 (1H, d, J = 1.3 Hz), 8.51 (1H, d, J = 1.3 Hz), 8.55 (1H, d, J = 7.8 Hz) |
| 7 | | 0.1 | 9-Cl | H | H | 6.51 (1H, d, J = 7.9 Hz), 7.75 (1H, d, J = 7.8 Hz), 8.27 (1H, d, J = 7.8 Hz), 8.57 (1H, d, J = 7.9 Hz) |
| 8 | | 16.5 | 8-t-Bu | CH₃ | C₄H₉ | 1.00 (3H, t, J = 7.4 Hz), 1.48 (9H, s), 1.53 (2H, m), 1.86 (2H, m), 2.37 (3H, s), 3.32 (2H, m), 8.44 (1H, d, J = 1.2 Hz), 8.46 (1H, d, J = 1.2 Hz) |
| 9 | | 10.5 | 8-t-Bu | H | CH₃ | 1.48 (9H, s), 2.89 (3H, d, J = 1.1 Hz), 6.26 (1H, d, J = 1.1 Hz), 8.43 (1H, d, J = 1.3 Hz), 8.46 (1H, d, J = 1.3 Hz) |
| 10 | | 18.6 | 8-t-Bu | CH₃ | C₆H₁₃ | 0.90 (3H, t, J = 7.1 Hz), 1.35 (4H, m), 1.48 (9H, s), 1.48 (2H, m), 1.87 (2H, m), 2.22 (3H, s), 3.32 (2H, t, J = 7.8 Hz), 8.44 (1H, d, J = 1.2 Hz), 8.46 (1H, d, J = 1.2 Hz) |

TABLE 1-continued

| Compound No. | Starting compound | Yield, % | R₁ | R₂ | R₃ | NMR (ppm), CDCl₃ |
|---|---|---|---|---|---|---|
| 11 | | 9.2 | 8-t-Bu | H | $C_2H_5$ | 1.48 (9H, s), 1.52 (3H, t, J = 7.5 Hz), 3.30 (2H, dq, J1 = 7.5 Hz, J2 = 1.0 Hz), 6.28 (1H, t, J = 1.0 Hz), 8.43 (1H, d, J = 1.2 Hz), 8.46 (1H, d, J = 1.2 Hz) |
| 12 | | 10.8 | 8-t-Bu | $CH_3$ | $C_2H_5$ | 1.49 (9H, s), 1.48 (3H, t, J = 7.5 Hz), 2.23 (3H, s), 3.36 (2H, q, J = 7.5 Hz), 8.44 (1H, d, J = 1.4 Hz), 8.46 (1H, d, J = 1.4 Hz) |
| 13 | | 3.9 | 8-s-Bu | $CH_3$ | $CH_3$ | 0.84 (3H, t, J = 7.3 Hz), 1.38 (3H, d, J = 6.8 Hz), 1.73 (2H, m), 2.21 (3H, d, J = 0.8 Hz), 2.94 (3H, d, J = 0.8 Hz), 2.96 (1H, m), 8.20 (1H, s), 8.21 (1H, s) |
| 14 | | 3.8 | 8-s-Bu | H | $CF_3$ | 0.86 (3H, t, J = 7.4 Hz), 1.39 (3H, d, J = 7.0 Hz), 1.65–1.81 (2H, m), 2.99 (1H, m), 7.00 (1H, s), 8.26 (1H, d, J = 0.9 Hz), 8.37 (1H, d, J = 0.9 Hz) |
| 15 | | 0.6 | 8-F | $CH_3$ | $C_2H_5$ | 1.42 (3H, t, J = 7.6 Hz), 2.15 (3H, s), 3.29 (2H, q, J = 7.6 Hz), 8.00 (1H, dd, J1 = 8.3 Hz, J2 = 1.9 Hz), 8.02 (1H, dd, J1 = 8.0 Hz, J2 = 1.9 Hz) |

TABLE 1-continued

| Compound No. | Starting compound | Yield, % | R₁ | R₂ | R₃ | NMR (ppm), CDCl₃ |
|---|---|---|---|---|---|---|
| 16 | | 0.9 | 8-n-Pen | CH₃ | C₂H₅ | 0.96 (9H, s), 1.49 (3H, t, J = 7.5 Hz), 2.26 (3H, s), 3.22 (2H, s), 3.36 (2H, q, J = 7.5 Hz), 8.13 (1H, d, J = 1.0 Hz), 8.14 (1H, d, J = 1.0 Hz) |
| 17 | | 11.6 | 8-t-Bu | CH₃ | C₃H₇ | 1.12 (3H, t, J = 7.5 Hz), 1.49 (9H, s), 1.93 (2H, m), 2.38 (3H, s), 3.31 (2H, t, J = 7.6 Hz), 8.45 (1H, d, J = 1.2 Hz), 8.46 (1H, d, J = 1.2 Hz) |
| 18 | | 1.6 | 8-t-Bu | CH₃ | i-Pr | 1.48 (9H, s), 1.69 (6H, d, J = 7.0 Hz), 2.26 (3H, s), 3.77 (1H, m), 8.44 (1H, d, J = 1.3 Hz), 8.46 (1H, d, J = 1.3 Hz) |
| 19 | | 2.1 | 8-t-Bu | C₂H₅ | C₂H₅ | 1.13 (3H, t, J = 7.5 Hz), 1.41 (9H, s), 1.45 (3H, t, J = 7.5 Hz), 2.65 (2H, q, J = 7.5 Hz), 3.26 (2H, q, J = 7.5 Hz), 8.37 (1H, d, J = 1.2 Hz), 8.39 (1H, d, J = 1.2 Hz) |
| 20 | | 2.7 | 8-i-Pr | CH₃ | C₂H₅ | 1.40 (6H, d, J = 7.1 Hz), 1.47 (3H, t, J = 7.6 Hz), 2.22 (3H, s), 3.26 (1H, m), 3.36 (2H, q, J = 7.6 Hz), 8.26 (1H, s), 8.27 (1H, s) |

TABLE 1-continued

| Compound No. | Starting compound | Yield, % | R₁ | R₂ | R₃ | NMR (ppm), CDCl₃ |
|---|---|---|---|---|---|---|
| 21 | (structure: 2-methyl-3-chloro-6-t-butyl quinolin-4(1H)-one) | 9.2 | 8-t-Bu | Cl | CH₃ | 1.50 (9H, s), 3.10 (3H, s), 8.51 (1H, d, J = 1.2 Hz), 8.55 (1H, d, J = 1.2 Hz) |
| 22 | (structure with n-C₃H₁₇ and s-Bu) | 1.1 | 8-s-Bu | CH₃ | C₈H₁₇ | 0.77 (3H, t, J = 7.5 Hz), 0.80 (3H, t, J = 6.4 Hz), 1.27–1.35 (8H, m), 1.37 (3H, d, J = 7.0 Hz), 1.50 (2H, m), 1.73 (2H, m), 1.86 (2H, m), 2.21 (3H, s), 2.95 (1H, m), 3.30 (2H, m), 8.20 (1H, s), 8.21 (1H, s) |
| 23 | (structure with isobutyl and t-Bu) | 13.8 | 8-t-Bu | CH₃ | CH₂CH(CH₃)₂ | 1.08 (6H, d, J = 6.5 Hz), 1.49 (9H, s), 2.22 (3H, s), 2.38 (1H, m), 3.22 (2H, d, J = 7.6 Hz), 8.46 (1H, d, J = 1.2 Hz), 8.47 (1H, d, J = 1.5 Hz) |
| 24 | (structure with ethyl and F₃CO) | 0.14 | 8-CF₃O | CH₃ | C₂H₅ | 1.49 (3H, t, J = 7.6 Hz), 2.33 (3H, s), 3.37 (2H, q, J = 7.6 Hz), 8.21 (1H, t, J = 0.8 Hz), 8.27 (1H, d, J = 0.8 Hz) |
| 25 | (structure with ethyl and Cl) | 0.4 | 8-Cl | CH₃ | C₂H₅ | 1.49 (3H, t, J = 7.6 Hz), 2.22 (3H, s), 3.35 (2H, q, J = 7.6 Hz), 8.30 (1H, d, J = 1.0 Hz), 8.38 (1H, d, J = 1.0 Hz) |

TABLE 1-continued

| Compound No. | Starting compound | Yield, % | R₁ | R₂ | R₃ | NMR (ppm), CDCl₃ |
|---|---|---|---|---|---|---|
| 26 | | 2.3 | 8-NO₂ 9-CH₃O | CH₃ | C₂H₅ | 1.48 (3H, t, J = 7.6 Hz), 2.23 (3H, s), 3.36 (2H, q, J = 7.6 Hz), 4.92 (3H, s), 8.83 (1H, s) |
| 27 | | 20.5 | 8-t-Bu | CH₃ | C₅H₁₁ | 0.92 (3H, t, J = 7.2 Hz), 1.32–1.45 (4H, m), 1.48 (9H, s), 1.88 (2H, m), 2.38 (3H, s), 3.32 (2H, t, J = 8.0 Hz), 8.44 (1H, d, J = 1.2 Hz), 8.46 (1H, d, J = 1.2 Hz) |
| 28 | | 14.6 | 8-t-Bu | CH₃ | C₇H₁₅ | 0.88 (3H, t, J = 7.0 Hz), 1.24–1.44 (8H, m), 1.48 (9H, s), 1.85 (2H, m), 2.17 (3H, s), 3.31 (2H, t, J = 8.0 Hz), 8.44 (1H, d, J = 1.2 Hz), 8.46 (1H, d, J = 1.4 Hz) |
| 29 | | 23.5 | 8-t-Bu | (CH₂)₄ | | 1.48 (9H, s), 1.89 (2H, m), 2.00 (2H, m), 2.69 (2H, m), 3.37 (2H, m), 8.44 (1H, d, J = 1.3 Hz), 8.45 (1H, d, J = 1.2 Hz) |
| 30 | | 14.5 | 8-t-Bu | (CH₂)₃ | | 1.49 (9H, s), 2.36 (2H, m), 2.99 (2H, m), 3.56 (2H, m), 8.45 (1H, d, J = 1.2 Hz), 8.49 (1H, d, J = 1.2 Hz) |

Production of harmful organism control agent
Harmful organism control agents were produced by the following methods from compound 1 synthesized above.
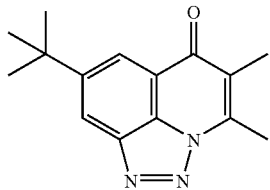
(Compound 1)
Harmful Organism Control Agent 1: Wettable Powder

The following ingredients were intimately mixed together according to the following formulation, and the mixture was ground to prepare wettable powder.

| | |
|---|---|
| Compound of invention (compound 1) | 25 wt. % |
| Clay | 30 wt. % |
| Diatomaceous earth | 35 wt. % |
| Calcium lignin sulfonate | 3 wt. % |
| Polyoxyethylene alkylaryl ether | 7 wt. % |

Harmful Organism Control Agent 2: Dust

The following ingredients were intimately mixed together according to the following formulation to prepare dust.

| | |
|---|---|
| Compound of invention (compound 1) | 2 wt. % |
| Clay | 60 wt. % |
| Talc | 37 wt. % |
| Calcium stearate | 1 wt. % |

Harmful Organism Control Agent 3: Emulsifiable Concentrate

The following ingredients were intimately mixed together according to the following formulation to dissolve them in one another. Thus, an emulsifiable concentrate was prepared.

| | |
|---|---|
| Compound of invention (compound 1) | 20 wt. % |
| N,N-Dimethylformamide | 20 wt. % |
| Xylene | 50 wt. % |
| Polyoxyethylene alkylaryl ether | 10 wt. % |

Harmful Organism Control Agent 4: Granules

The following ingredients were homogeneously ground and intimately mixed together according to the following formulation. Water was added to the mixture, followed by thorough kneading. Thereafter, the kneaded product was granulated and dried to prepare granules.

| | |
|---|---|
| Compound of invention (compound 1) | 5 wt. % |
| Bentonite | 40 wt. % |
| Talc | 53 wt. % |
| Calcium lignin sulfonate | 2 wt. % |

Evaluation Test

Compounds 1 to 30 of the present invention thus prepared were subjected to the following evaluation tests.

Test 1: Control Effect Against *Tetranychus cinnabarinus*

A kidney leaf disk having a diameter of 2 cm was placed on agar. Ten female adult mites of *Tetranychus cinnabarinus* were released on the kidney leaf disk. The mites were allowed to oviposit in a chamber kept at a constant temperature (25° C.) for 24 hr. The female adult mites were then removed from the kidney leaf disk. The compound of the present invention, which had been diluted to a concentration of 100 ppm by the addition of a spreader (Tween 20), was spread over the kidney leaf disk by means of a spray gun.

Seven days after the treatment, the test system was observed for hatching of eggs and survival or death of larval mites and nymphs, and the unhatching rate of eggs and the death rate of larval mites/nymphs were calculated based on the observation results. The sum of the unhatching rate of eggs and the death rate of larval mites/nymphs was determined as the total death rate.

The following compounds had an activity of not less than 80% in terms of total death rate:

Compounds 1, 12, 16, 17, 18, and 20.

Test 2: Pesticidal Effect Against *Plutella xylostella*

A cabbage leaf disk having a diameter of 5 cm was placed in a plastic cup. The compound of the present invention, which had been diluted to a concentration of 100 ppm by the addition of a spreader (Tween 20), was spread over the cabbage leaf disk by means of a spray gun, and the cabbage leaf disk was then air dried. Ten larvae at the second instar of *Plutella xylostella* were released in the cup. The cup was then lidded, and the larvae were reared in a chamber at a constant temperature (25° C.).

Three days after the treatment, the larvae were observed for survival or death, and the death rate of larvae was calculated based on the observation results.

The following compounds had an activity of not less than 80% in terms of death rate:

Compounds 1, 4, 12, 13, 16, 18, 20, 25, and 30.

Test 3: Pesticidal Effect Against *Spodoptera litura*

A cabbage leaf disk having a diameter of 5 cm was placed in a plastic cup. The compound of the present invention, which had been diluted to a concentration of 100 ppm by the addition of a spreader (Tween 20), was spread over the cabbage leaf disk by means of a spray gun, and the cabbage leaf disk was then air dried. Five larvae at the third instar of *Spodoptera litura* were released in the cup. The cup was then lidded, and the larvae were reared in a chamber at a constant temperature (25° C.).

Three days after the treatment, the larvae were observed for survival or death, and the death rate of larvae was calculated based on the observation results.

The following compounds had an activity of not less than 80% in terms of death rate:

Compounds 1, 12, 16, 18, 20, 25, and 30.

Test 4: Pesticidal Effect Against *Myzus persicae*

A cabbage leaf disk having a diameter of 5 cm was placed in a plastic cup. The compound of the present invention, which had been diluted to a concentration of 100 ppm by the addition of a spreader (Tween 20), was spread over the cabbage leaf disk by means of a spray gun, and the cabbage leaf disk was then air dried. Ten larvae at the first instar of *Myzus persicae* were released in the cup. The cup was then lidded, and the larvae were reared in a chamber at a constant temperature (25° C.).

Three days after the treatment, the larvae were observed for survival or death, and the death rate of larvae was calculated based on the observation results.

The following compounds had an activity of not less than 80% in terms of death rate:

Compounds 1, 3, 4, 12, 13, 16, and 18.

Test 5: Control Effect Against Cucumber Downy Mildew

A potting compost (an equivalent of a commercially available product) was placed in plastic pots, and seed cucumber (variety: Su-yo) was inoculated into potting compost in the pots. The seed cucumber was cultivated for about 10 days to provide young cucumber plants in which seed leaves had been fully developed. The cucumber plants were used as sample plants.

The compound of the present invention, which had been diluted to a concentration of 200 ppm by the addition of a spreader (Neoesterin), was applied in an amount of 5 ml per 3 pots by means of a spray gun and was air dried. Next, a conidial suspension ($1 \times 10^6$ to $5 \times 10^6$ spores/ml) prepared from conidia collected from cucumber leaves, which had been previously diseased by inoculating *Pseudoperonospora cubensis*, was spray inoculated homogeneously into the pots, and the pots were left to stand in a moist chamber of 21° C. for 24 hr. Thereafter, the pots were transferred to an environment control room kept at 18° C. at night and at 22° C. in the daytime to induce the disease.

Seven days after the inoculation, the disease developed area of the seed leaf was measured and is indexed according to the following criteria to judge the state of disease development.

| State of disease development in seed leaf | Disease development index |
|---|---|
| No lesion | 0 |
| A few lesions | 1 |
| Disease developed area of less than quarter of leaf area | 2 |
| Disease developed area of quarter to less than half of leaf area | 3 |
| Disease developed area of half to less than three quarters of leaf area | 4 |
| Disease developed area of not less than three quarters of leaf area | 5 |

Next, the results were included in the following equations to calculate the disease development rate and the protective value.

[Disease development rate]=Σ(index×number of relevant roots)/(number of examined roots×5)×100

[Protective value]=(1−disease development rate in treated plot/disease development rate in nontreated plot)×100

As a result, the following compounds had an activity of not less than 80 in terms of protective value:

Compounds 1, 9, 11, 12, 13, 14, 17, 18, 20, 21, 25, and 30.

Test 6: Control Effect Against Rice Blast

A potting compost (an equivalent of a commercially available product) was placed in plastic pots, and seed rice (variety: Jukkoku) was inoculated into potting compost in the pots. The seed rice was cultivated for about 15 days to provide young rice plants in which the fourth leaf had been fully developed. The rice plants were used as sample plants.

The compound of the present invention, which had been diluted to a concentration of 100 ppm by the addition of a spreader (Neoesterin), was applied in an amount of 10 ml per 3 pots by means of a spray gun and air dried. Next, a conidial suspension ($1 \times 10^6$ to $5 \times 10^6$ spores/ml) prepared from conidia collected from a Petri dish, in which *Pyricularia oryza* had been previously cultivated, was spray inoculated homogeneously into the pots, and the pots were left to stand in a moist chamber of 25° C. for 24 hr. Thereafter, the pots were transferred to an environment control room kept at 20° C. at night and at 25° C. in the daytime to induce the disease.

Seven days after the inoculation, the number of lesions in the fourth leaf in the treated plot and the number of lesions in the fourth leaf in the nontreated plot were counted, and the results were included in the following equation to calculate the protective value.

[Protective value]=(1−number of lesions in treated plot/number of lesions in nontreated plot)×100

As a result, the following compounds had an activity of not less than 80 in terms of protective value:

Compounds 1, 2, 14, and 26.

What is claimed is:

1. A compound of formula (1) or a salt thereof:

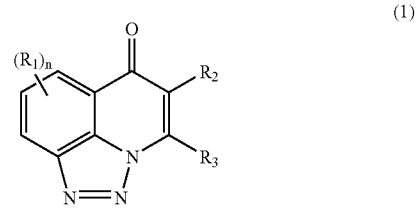

(1)

wherein

R$_1$, which may be the same or different, represent(s) a halogen atom; straight chain, branched chain, or cyclic C1–6 alkyl optionally substituted by a halogen atom or hydroxyl; straight chain or branched chain C1–6 alkoxy optionally substituted by a halogen atom or hydroxyl; or nitro, n is an integer of 0 (zero) to 3, R$_2$ represents a hydrogen atom; a halogen atom; or straight chain, branched chain, or cyclic C1–4 alkyl optionally substituted by a halogen atom or hydroxyl, and R$_3$ represents a hydrogen atom; a halogen atom; or straight chain, branched chain, or cyclic C1–12 alkyl optionally substituted by a halogen atom or hydroxyl, or R$_2$ and R$_3$ together may represent —(CH$_2$)$_m$— wherein m is an integer of 3 or 4;

excluding the compound of formula (1) wherein n is 0, R$_2$ represents a hydrogen atom, and R$_3$ represents methyl.

2. The compound of formula (1) according to claim 1 or a salt thereof, wherein formula (1) is represented as formula (1')

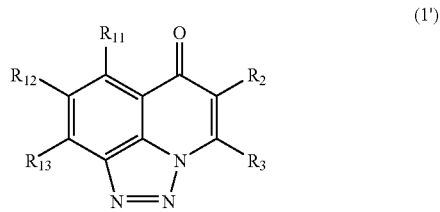

(1')

wherein

R$_{11}$ represents a hydrogen atom, and

R$_{12}$ and R$_{13}$ each independently represent a hydrogen atom; a halogen atom; straight chain, branched chain, or cyclic C1–6 alkyl optionally substituted by a halogen atom; straight chain, or branched chain, C1–6 alkoxy optionally substituted by a halogen atom; or nitro.

3. A process for producing the compound of formula (1) according to claim 1, said process comprising the steps of:

nitrating a compound of formula (2)

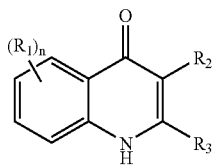

(2)

wherein

R$_1$, which may be the same or different, represent(s) a halogen atom; straight chain, branched chain, or cyclic C1–6 alkyl optionally substituted by a halogen atom or hydroxyl; straight chain or branched chain C1–6 alkoxy optionally substituted by a halogen atom or hydroxyl; or nitro, n is an integer of 0 (zero) to 3, R$_2$ represents a hydrogen atom; a halogen atom; or straight chain, branched chain, or cyclic C1–4 alkyl optionally substituted by a halogen atom or hydroxyl, and R$_3$ represents a hydrogen atom; a halogen atom; or straight chain, branched chain, or cyclic C1–12 alkyl optionally substituted by a halogen atom or hydroxyl, or R$_2$ and R$_3$ together may represent —(CH$_2$)$_m$— wherein m is an integer of 3 or 4, to give a compound of formula (3)

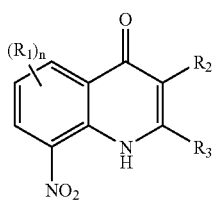

(3)

wherein R$_1$, n, R$_2$, and R$_3$ are as defined in formula (2);

reducing the compound of formula (3) to give a compound of formula (4)

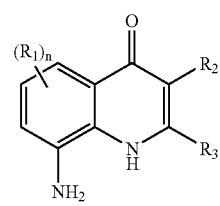

(4)

wherein R$_1$, n, R$_2$, and R$_3$ are as defined in formula (2); and diazotizing the compound of formula (4) to give the compound of formula (1).

4. A harmful organism control composition comprising as an active ingredient at least one compounds according to claim 1 or salt thereof, and a carrier or adjuvant.

5. A method for controlling a harmful organism, comprising the step of treating a plant, which has been damaged by a harmful organism or has a fear of being damaged by a harmful organism, with a compound of formula (1) or a salt thereof:

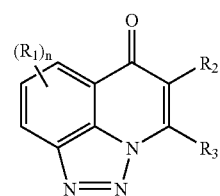

(1)

wherein

R$_1$, which may be the same or different, represent(s) a halogen atom; straight chain, branched chain, or cyclic C1–6 alkyl optionally substituted by a halogen atom or hydroxyl; straight chain or branched chain C1–6 alkoxy optionally substituted by a halogen atom or hydroxyl; or nitro, n is an integer of 0 (zero) to 3, R$_2$ represents a hydrogen atom; a halogen atom; or straight chain, branched chain, or cyclic C1–4 alkyl optionally substituted by a halogen atom or hydroxyl, and R$_1$ represents a hydrogen atom; a halogen atom; or straight chain, branched chain, or cyclic C1–12 alkyl optionally substituted by a halogen atom or hydroxyl, or R$_2$ and R$_3$ together may represent —(CH$_2$)$_m$— wherein m is an integer of 3 or 4.

6. The compound of formula (1) according to claim 1 or a salt thereof, wherein n of formula (1) is an integer of 1 to 3.

* * * * *